United States Patent [19]

Erickson

[11] 4,444,830
[45] Apr. 24, 1984

[54] METHOD FOR PREPARING ABSORBENT FIBROUS FLUFF

[75] Inventor: Robert E. Erickson, Midland, Mich.

[73] Assignee: The Dow Chemical Company, Midland, Mich.

[21] Appl. No.: 336,540

[22] Filed: Jan. 4, 1982

[51] Int. Cl.$^3$ .............................................. D03D 3/00
[52] U.S. Cl. ..................... 428/246; 156/153; 241/28; 264/118; 428/248; 428/284; 428/286; 428/913; 604/368; 604/378
[58] Field of Search ...................... 241/28, 30; 19/305, 19/306; 427/289; 156/153; 428/246, 248, 284, 286, 913; 264/118; 128/287, 290 R, 296; 524/35, 45; 604/368, 378

[56] References Cited

U.S. PATENT DOCUMENTS

| | | | |
|---|---|---|---|
| 3,658,613 | 4/1972 | Steiger | 128/296 |
| 3,888,257 | 6/1975 | Cook et al. | 128/290 R |
| 3,959,569 | 5/1976 | Burkholder | 427/195 |
| 3,966,679 | 6/1976 | Gross | 427/386 |
| 4,018,951 | 4/1977 | Gross | 427/401 |
| 4,076,928 | 2/1978 | Gross | 526/304 |
| 4,079,029 | 3/1978 | Gross | 428/255 |
| 4,117,184 | 9/1978 | Erickson | 428/340 |

*Primary Examiner*—James J. Bell
*Attorney, Agent, or Firm*—A. R. Lindstrom

[57] ABSTRACT

A method of preparing fibrous hydrophilic fluff having increased absorbency is disclosed. An absorbent polymer solution is coated on base fluffing material, and the coated fluffing material is dried, disintegrated and mechanically worked into a fibrous fluff matrix which contains absorbent polymer platelets distributed throughout said matrix.

24 Claims, No Drawings

METHOD FOR PREPARING ABSORBENT FIBROUS FLUFF

BACKGROUND OF THE INVENTION

This invention relates to fibrous hydrophilic fluff and a method of preparing said fluff wherein an aqueous solution of polymer is formulated into an absorbent composition and then coated on the base fluffing material. The absorbent coated base fluffing material composite is then disintegrated and worked by mechanical means into a plurality of fluff fibers having a high absorption and retention rate.

There are numerous disposable articles in the form of diapers, tampons and the like available on the market which contain a central matrix of absorbent fibrous fluff having varying degrees of absorbency. There are, as well, a large variety of disposable absorbent pads used in institutions such as hospitals including underpads as well as adult and junior diapers. For example, U.S. Pat. No. 3,888,257 illustrates a disposable absorbent article utilizing a powdered polymer dispersed in a wicking substrate useful for the same general purposes as the articles which contain the absorbent hydrophilic fluff of this invention. Fiberized wood pulp alone is not highly efficient. In order to enhance the absorbency of the fiberized wood pulp, water-absorbent polymers have been proposed for distribution within the absorbent matrix.

The conventional fluff matrix construction of the prior known art was fibrous fluff which had been treated with finely divided powdered absorbent polymer. In this regard it has been found that application of the powdered absorbent polymer presented special problems of distribution within the cell matrix, as well as special problems in application. The finely divided powder is very difficult to maintain in anhydrous form while applying it to the fibrous fluff matrix. Presently, the accepted industry practice is to construct a substantially closed system of application in order to minimize the particulate dust which would emanate from the application site. Elaborate systems have been designed for the purpose of containing the absorbent particle dust, yet even a small amount of absorbent powder escaping from the substantially closed system requires special clean-up and maintenance procedures. When the powdered absorbent of the prior known art came in contact with moisture in the plant's atmosphere, it immediately began to swell, thereby yielding a gel which was not easily cleansed away due to its water-absorbent properties. Thus, special solvents were required to maintain the equipment, and more significantly, the surrounding area in which the powdered absorbent dust settled.

The patent to R. E. Erickson et al., U.S. Pat. No. 4,117,184, discloses an absorbent polymer composition having a lightly cross-linked carboxylic polyelectrolyte which has an enhanced absorbent capacity. The difficulty has been in finding a method of evenly distributing the absorbent polymer throughout the fluff matrix. One additional problem has been distributing a sufficient quantity of absorbent polymer into the fluff matrix in order to prepare resultant fluff products with improved absorbent qualities.

SUMMARY OF THE INVENTION

An aqueous polymer solution is formulated into an absorbent composition and coated on a base fluffing material. The absorbent polymer coated base fluffing material is mechanically disintegrated and worked to yield a fibrous hydrophilic fluff of enhanced absorbency and which contains a substantially even distribution of absorbent polymer throughout the fibrous fluff matrix. Further, the present invention comprises a water-swellable absorbent which is a composite fluff of absorbent polymer and base fluffing material. The base fluff material can be selected from a group of those articles which contain a fiber matrix capable of being mechanically disintegrated and worked into a fluff. The fluff base material may include the more common fluff pulp board which can be mechanicaly worked to prepare a fiberized wood pulp.

Hydrophilic absorbent fluff is characterized by being rapidly wetted and swelled by water and comprises a lightly cross-linked carboxylic electrolyte which has been intimately distributed within the fibrous fluff matrix by mechanical means.

DETAILED DESCRIPTION OF THE INVENTION

For purposes of this invention, the following terms have the prescribed meaning.

By "fluff" is meant any wicking substrate which has been mechanically worked and disintegrated into a matrix of discontinuous wicking fibers having a plurality of zones wherein the absence of fibrous matter imports air pockets with varying degrees of uniformity thus producing a loose, soft mass of fibers.

By "absorbent fluff" is meant any absorbent matrix which has been prepared by disintegration and mechanically working absorbent polymer coated base fluffing material in accordance with the spirit and teachings of the present invention. More precisely, the absorbent fluff matrix contains an intimate dispersion of absorbent polymer, distributed within the fibrous fluff matrix by mechanical disintegration and working of the absorbent polymer coated base fluffing material in a mechanical fluffing chamber.

By "base fluffing material" is meant a compacted mass of fibrous material which, when mechanically worked, is capable of forming a loose, soft mass of fibers herein described as fluff.

Absorbent polymers useful in the practice of this invention generally may be any physiologically compatible, water-insoluble hydrophilic polymer which is capable of formulation into a coating solution. An embodiment of the present invention utilizes an aqueous solution of a lightly cross-linked alkali metal carboxylic polyelectrolyte.

The preferred hydrophilic polymers useful in this invention are polyelectrolytes exemplary of which are ammonium or alkali metal salts of homopolymers of acrylic or methacrylic acid and copolymers with one or more ethylenically unsaturated comonomers.

Preferably, the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl group has from 1 to 4 carbons.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxyethyl acrylate and 4-hydroxybutyl acrylate.

The olefinically unsaturated carboxylic acids useful in this invention are mono- or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows: acrylic acid - acrylate copolymers; acrylic acid - acrylamide copolymers; acrylic acid - olefinic copolymers; polyacrylic acid; acrylic acid - vinyl aromatic copolymers; acrylic vinyl ether copolymers; acrylic acid - vinyl acetate copolymers; acrylic acid - vinyl alcohol copolymers and copolymers of methacrylic acid with all the above comonomers.

Illustrative examples of the polyfunctional cross-linking agents useful in this invention to convert the above polyelectrolytes into water-swellable polymers are set forth in U.S. Pat. Nos. 2,929,154; 3,224,986; and 3,332,909. These polyfunctional cross-linking agents are generally known as polyamidepolyamine epichlorohydrin adducts. The disclosure of these references are incorporated herein by reference. Similar cross-linking agents are also commercially available from Hercules Incorporated as Kymene 557 and Polycup 172. The structure of these adducts has been discussed in an article by M. E. Coor et al., Journal of Applied Polymer Science, Vol. 17, pages 721-735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as cross-linking agents are monomeric amine-epihalohydrin adducts prepared by reacting at least two moles of an epihalohydrin with one mole of various monoamines, diamines and triamines at a temperature in the range from 0° to 90° C. for a time period of 0.5 to .8 hours. The reaction is carried out in a reaction media containing 20 to 90 percent water, lower alcohols such as methanol or ethanol, or in aqueous solutions of the lower alcohols. The amino-epihalohydrin adducts are used directly as made without separation or concentration. The preparation and use of amino-epihalohydrin adducts as cross-linking agents is further disclosed in the patent application by J. R. Gross, Ser. No. 219,072 filed Dec. 22, 1980. This application is incorporated by reference herein.

Sulfonium zwitterions are known from U.S. Pat. Nos. 3,660,431; 3,749,737; and 3,749,738. The disclosure of these patents are incorporated herein by reference.

These cross-linking agents are used in an amount from about 0.05 to about 5.0 percent based on the weight of the polyelectrolyte used. This is generally sufficient to cause the polyelectrolyte to become lightly cross-linked.

Other hydrophilic polymers may also be employed, such as acrylic copolymer and starch/graft copolymers. Composites containing such polymers with wicking substrates are available commercially as Permasorb Sheet Laminate and Sanwet 1M-300. Also useful are the water-insoluble alkali salts of saponified, gelatinized starch/polyacrylonitrile graft polymers taught in U.S. Pat. Nos. 3,997,484 and 4,405,387. Other such polymers will be known.

For the purpose of this invention, a moisture absorbent or water-swellable polyelectrolyte or polymer is defined as one which absorbs greater than about 15 times its weight of synthetic or natural urine. Preferably, the absorbency should be in the range from about 30-60 grams of urine per gram of polyelectrolyte or in the range of 90-250 grams of deionized water per gram of polyelectrolyte. The level of cross-linking agent used is a variable factor which is dependent upon the particular polyelectrolyte used and the molecular weight of the polyelectrolyte. Preferably, the amount used varies from the 0.25 to 3.0 percent based on the weight of the polyelectrolyte. However, this range is varied for each polyelectrolyte in order to adjust the absorbency of the final cross-linked material.

It is sometimes desirable to add a small amount of a surfactant to the polyelectrolyte composition to aid in flowing the solution onto the base fluffing material. A secondary benefit of using a surfactant is to increase the wettability of the final dry absorbent fluff. Either anionic or nonionic surfactants may be used.

The aqueous polymer solution is coated on the base fluffing material by conventional means such as spraying, reverse roll coating, etc., and preferably doctored to uniform thickness with a drawbar, air knife or similar means. The coating is dried and the dried coated substrate then disintegrated into the absorbent fluff. The severity of the applied stress and the mechanical parameters are readily adjusted to optimum with single preliminary experiments.

One method of increasing the amount of absorbent polymer present in the fluff matrix is to increase the absorbent polymer film thickness on the base fluffing material. The thickness of the coating film can vary greatly, so long as the coated base fluffing material is still capable of being disintegrated and mechanically worked into an absorbent fibrous fluff. It can be seen that feeding coated base fluffing material having a specified thickness of polymer film coating and a known amount of base fluffing material, will yield an absorbent fibrous fluff having an absorbent polymer to wicking substrate fluff ratio which can be desirably tailored to the manufacturer's product specification. Exact amounts of absorbent polymer and base fluffing material needed can be determined by simple arithmetic calculation once the desired absorbent polymer content of the resultant fluff has been determined.

An optional embodiment available with the method is the concurrent disintegration of an absorbent composite and a base fluffing material. In that instance, it is only necessary that the composite and base fluffing material be added to the disintegrator in whatever predetermined ratio is desired in the resulting fluff. This option permits an easy adjustment of the amount of wicking substrate in the final fluff and can be achieved without shutting down the apparatus. The composite fluff exhibits a high absorption capacity, in economical fashion. In this regard, as indicated above, the distribution of hydrophilic absorbent polymer within the absorbent matrix, unlike that of the known prior art, is accomplished in a uniform, intimately dispersed manner.

The resulting fluff is well suited for use in known absorbent devices. The fluff may be blended with other fluff or may be employed in a layered structure with fibrous fluff.

The method of this invention permits production of fluff having an absorbent polymer bonded to fibers of the fluff and being uniformly distributed throughout the fluff. The method permits quick and easy adjustment of the ratio of absorbent polymer to fibrous fluff. The method minimizes the amount of polymer lost during preparation as is a common problem in the use of granular polymers added to a fluff. In this regard, it is noted that even that polymer which is flaked off during disintegration is in the form of platelets entrapped in the fibrous matrix. Much of the spherical granules of the prior used dry powders would sift through the matrix and be lost. Because less polymer is lost during production, clean up operations are simplified.

The invention is illustrated in the following examples.

EXAMPLE 1

The solution of acrylic polymer is formulated into the absorbent coating having Composition 1 as follows:

The acrylic polymer was the polymerizate of 52 mole percent ethyl acrylate, 28 mole percent sodium methacrylate, and 20 mole percent sodium acrylate having a pH of 6 to 8.

94.0 Weight percent of that acrylic polymer is combined in solution with 5.0 weight percent polyoxyethylene sorbitan monolaurate and 1.0 weight percent polyamide/epichlorohydrin resin. This composition is coated on 120 lb/1000 ft$^2$ (0.5 kg/m$^2$) fluff pulp board using a No. 70 Meyer rod (wire wound rod) to a dry coating weight of 8.8 grams (dry weight)/ft.$^2$ (0.818 g/m$^2$). The coated board was dried for 10 minutes at about 250° F. (120° C.) in a hot air oven. The coated board was cut into small pieces and converted to a fluff using a commercial blender. The fluff containing this composition was checked for absorbent capacity by placing 1 gram of fluff in 150 cubic centimeters of 1 percent sodium chloride solution, allowed to soak for 30 minutes, filtered through 150 mesh nylon screen, collected and then the filtrate was weighed. The result of this test is given in Table I.

EXAMPLE 2

The aqueous solution of acrylic polymer is formulated into the absorbent coating having Composition 2 as follows:

94.4 Weight percent of acrylic polymer is combined with 5.0 weight percent of polyoxyethylene sorbitan monolaurate and 0.6 weight percent polyamide/epichlorohydrin resin. This composition is processed and tested according to the procedures of Example 1. The results of this test are given in Table I.

EXAMPLE 3

The aqueous solution of acrylic polymer is formulated into the absorbent coating having Composition 3 as follows:

71.5 Weight percent of acrylic polymer is combined with 1.0 weight percent polyoxyethylene sorbitan monolaurate, 0.5 weight percent polyamide/epichlorohydrin resin, and 27.0 weight percent glycerine. This composition is processed and tested according to the procedures of Example 1. The result of this test is given in Table I.

TABLE I

|  | Polymer in Fluff | Absorbency Capacity |
| --- | --- | --- |
| Composition 1 | 14% | 20 grams/gram of fluff |
| Composition 2 | 14% | 25 grams/gram of fluff |
| Composition 3 | 14% | 19 grams/gram of fluff |
| Uncoated Fluff | — | 16 grams/gram of fluff |

Compositions 1, 2 and 3 were coated on a heavier weight fluff pulp board (154 lbs/1000 ft$^2$ or 0.75 Kg/m$^2$) and the results were similar to those stated in Table I.

EXAMPLE 4

A pilot coating run was made using a Keegan Coater. Fluff pulp board weighing 160 lbs/1000 ft$^2$ (0.78 Kg/m$^2$) was coated with Composition 1 using a modified wire wound rod as the coating head. The oven temperature was 350° F. (176.7° C.) and the coated board was exposed in the oven for about 3 to 5 minutes until it was dry. The dry weight of the absorbent polymer coating was approximately 10 grams/ft$^2$ (0.929 g/m$^2$).

The coated board was converted to fluff using a commercial blender. Samples of fluff containing absorbent polymer were compared to uncoated fibrous fluff for absorbent capacity in 1 percent sodium chloride solution. Results are shown in Table II.

TABLE II

|  | Polymer in Fluff | Absorbent Capacity |
| --- | --- | --- |
| Pilot coated fluff board | 13.7% | 19.2 grams/gram fluff |
| Uncoated fluff | — | 16.3 grams/gram fluff |

Both Table I and II demonstrates the increased capacity of the cellulose fluff containing the absorbent polymer. An additional advantage of the absorbent polymer is its ability to retain the aqueous fluid under pressure to a greater extent than fluff in the prior art.

For purposes of this invention the absorbent composition can be varied considerably in degree of cross-linking, polymer content, surfactants, pigments and fillers, and other desired ingredients which the skilled artisan would include in conventional amounts. In addition, a high molecular weight, slightly cross-linked salt form of acrylic acid could be used although associated with it would be the high cost of removing water. A drying step can be accomplished with conventional drying equipment such as a steam heated drying drum, microwave heaters, infrared heaters, or similar equipment. The preferred drying temperature is about 250° F. (120° C.) and for sufficient time to remove all of the moisture from the coated board. Temperature ranges from 150° F. (65.6° C.) to 350° F. (176.7° C.) can be used with appropriate time periods to remove the moisture.

What is claimed is:

1. A method for preparing a fibrous fluff of improved absorbency, said method comprising passing a base fluffing material through a zone wherein an aqueous solution of polymer which has been formulated into an absorbent composition is coated on the base fluffing material, the absorbent coated base fluffing material composite is then dried and finally disintegrated and worked by mechanical means into a plurality of absorbent fluff fibers.

2. The method of claim 1 wherein the aqueous solution of absorbent polymer comprises an aqueous solution of a lightly cross-linked alkali metal carboxylic polyelectrolyte.

3. The method of claim 2 wherein the polyelectrolyte is cross-linked with a polyfunctional or difunctional cross-linking agent that is reactive with carboxylate groups.

4. The method of claim 3 wherein the polyfunctional cross-linking agent is a polyamide-polyamine epichlorohydrin adduct.

5. The method of claim 3 wherein the polyfunctional cross-linking agent is a diglycidyl ether.

6. The method of claim 2 wherein the polyelectrolyte consists of an alkali metal salt of a polyacrylate.

7. The method of claim 2 wherein the polyelectrolyte consists of a terpolymer of ethyl acrylate, sodium acrylate and sodium methacrylate with 50 mole percent being ethyl acrylate.

8. A method of claim 7 wherein the polyelectrolyte comprises a 25 percent aqueous solution by volume consisting of 52 mole percent ethyl acrylate, 28 mole percent sodium methacrylate, and 28 mole percent sodium acrylate, and having a pH range of from about 6 to about 8.

9. The method of claim 1 wherein the absorbent composition comprises a solution consisting of acrylic terpolymer, polyoxyethylene sorbitan monolaurate, polyamide/epichlorohydrin resin and glycerine.

10. The method of claim 9 wherein the absorbent composition comprises a solution of from about 71.5 to about 94.4 weight percent acrylic polymer, from about 5 to about 1 weight percent polyoxyethylene sorbitan monolaurate, from about 1.0 to about 0.6 weight percent polyamide epichlorohydrin resin, and from 0 to about 27.0 weight percent glycerine.

11. A method of claim 1 wherein the drying temperature range is from about 150° F. to about 350° F.

12. A method of claim 4 wherein the drying temperature is about 250° F.

13. The absorbent fluff prepared according to the method of claim 1.

14. The absorbent fluff prepared according to the method of claim 2.

15. An absorbent device which comprises the absorbent fluff of claim 13, a water-impermeable bottom sheet and a water-permeable face sheet.

16. An absorbent device which comprises the absorbent fluff of claim 13, one or more layers of intermediate wicking sheets, a water-impermeable bottom sheet and a water-permeable face sheet.

17. An absorbent device which comprises the absorbent fluff of claim 14, a water-impermeable bottom sheet and a water-permeable face sheet.

18. An absorbent device which comprises the absorbent fluff of claim 14, one or more layers of intermediate wicking sheets, a water-impermeable bottom sheet and a water-permeable face sheet.

19. The absorbent device of claim 15 wherein said water-impermeable bottom sheet comprises a flexible hydrophilic absorbent laminate having a central, substantially continuous and uniform film consisting of a lightly cross-linked carboxylic polyelectrolyte and a layer of wicking substrates bonded to both sides of said film.

20. The absorbent device of claim 17 wherein said water-impermeable bottom sheet comprises a flexible hydrophilic absorbent laminate having a central, substantially continuous and uniform film consisting of a lightly cross-linked carboxylic polyelectrolyte and a layer of wicking substrates bonded to both sides of said film.

21. The absorbent device of claim 19 wherein said water-impermeable bottom sheet is polyethylene and said face sheet is a nonwoven fiber mat.

22. The absorbent device of claim 20 wherein said water-impermeable bottom sheet is polyethylene and said face sheet is a nonwoven fiber mat.

23. The absorbent device of claim 19 wherein said intermediate wicking sheets are selected from a group consisting of woven fabrics, paper tissues, nonwoven fiber mats, polymeric foams, and flexible hydrophilic absorbent laminate.

24. The absorbent device of claim 20 wherein said intermediate wicking sheets are selected from a group consisting of woven fabrics, paper tissues, nonwoven fiber mats, polymeric foams, and flexible hydrophilic absorbent laminates.

* * * * *